(12) United States Patent
Furuhata (10) Patent No.: US 10,419,704 B2
(45) Date of Patent: Sep. 17, 2019

(54) ENDOSCOPE DEVICE AND METHOD FOR CONTROLLING DISPLAY CHANGE IN ENDOSCOPE DEVICE

(71) Applicant: OLYMPUS CORPORATION, Tokyo (JP)

(72) Inventor: Tsuyoshi Furuhata, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 125 days.

(21) Appl. No.: 15/686,877

(22) Filed: Aug. 25, 2017

(65) Prior Publication Data
US 2017/0353687 A1  Dec. 7, 2017

Related U.S. Application Data

(63) Continuation of application No. PCT/JP2016/072006, filed on Jul. 27, 2016.

(30) Foreign Application Priority Data

Sep. 3, 2015 (JP) .................................. 2015-173966

(51) Int. Cl.
*A61B 1/00* (2006.01)
*H04N 5/44* (2011.01)
(Continued)

(52) U.S. Cl.
CPC ......... *H04N 5/4403* (2013.01); *A61B 1/0005* (2013.01); *A61B 1/00009* (2013.01);
(Continued)

(58) Field of Classification Search
CPC .............. A61B 1/00045; A61B 1/0005; A61B 1/00048; H04N 5/4403; G02B 23/24
See application file for complete search history.

(56) References Cited

U.S. PATENT DOCUMENTS 5,825,502 A * 10/1998 Mayer .................. A61B 5/0059
                                                           358/296
6,339,446 B1 * 1/2002 Miyoshi ............... A61B 1/0005
                                                           348/65
(Continued)

FOREIGN PATENT DOCUMENTS

EP       2 008 574 A1    12/2008
EP       2 149 331 A1     2/2010
(Continued)

OTHER PUBLICATIONS

International Search Report dated Nov. 1, 2016 received in PCT/JP2016/072006.

*Primary Examiner* — Robert J Hance
(74) *Attorney, Agent, or Firm* — Scully, Scott, Murphy & Presser, P.C.

(57) ABSTRACT

An endoscope device having: a display configured to display a first image region and a second image region; and a controller configured to: perform first display change control to control the display to change a display state of the first image region based on an instruction input to an instruction input device through a first operation method; and perform second display change control to control the display to change a display state of the second image region based on an instruction input to the instruction input device through a second operation method.

11 Claims, 9 Drawing Sheets

(51) Int. Cl.
*G02B 23/24* (2006.01)
*A61B 1/04* (2006.01)
*H04N 5/232* (2006.01)
*H04N 5/445* (2011.01)
*G06F 3/0484* (2013.01)
*G06F 3/0485* (2013.01)
*G06F 3/0488* (2013.01)
*H04N 5/225* (2006.01)

(52) U.S. Cl.
CPC ...... *A61B 1/00039* (2013.01); *A61B 1/00045* (2013.01); *A61B 1/00048* (2013.01); *A61B 1/04* (2013.01); *G02B 23/24* (2013.01); *G06F 3/0485* (2013.01); *G06F 3/04842* (2013.01); *G06F 3/04845* (2013.01); *H04N 5/23216* (2013.01); *H04N 5/23293* (2013.01); *H04N 5/23296* (2013.01); *H04N 5/44504* (2013.01); *G06F 3/04883* (2013.01); *G06F 2203/04806* (2013.01); *H04N 2005/2255* (2013.01)

(56) References Cited

U.S. PATENT DOCUMENTS

| | | | |
|---|---|---|---|
| 10,092,165 B2 * | 10/2018 | Power | A61B 1/0005 |
| 2003/0001949 A1 * | 1/2003 | Obata | H04N 1/32128 |
| | | | 348/61 |
| 2005/0228221 A1 * | 10/2005 | Hirakawa | A61B 1/00009 |
| | | | 600/101 |
| 2006/0015012 A1 | 1/2006 | Sato | |
| 2007/0203413 A1 * | 8/2007 | Frangioni | A61B 5/415 |
| | | | 600/478 |
| 2009/0043157 A1 * | 2/2009 | Hirakawa | A61B 1/00045 |
| | | | 600/109 |
| 2009/0303316 A1 * | 12/2009 | Iwasaki | A61B 1/00022 |
| | | | 348/65 |
| 2010/0030021 A1 | 2/2010 | Minai et al. | |
| 2010/0317920 A1 * | 12/2010 | Doi | A61B 1/00045 |
| | | | 600/109 |
| 2011/0160578 A1 * | 6/2011 | Tripathi | A61B 90/37 |
| | | | 600/427 |
| 2012/0004529 A1 * | 1/2012 | Tolkowsky | G06T 19/20 |
| | | | 600/407 |
| 2012/0065469 A1 * | 3/2012 | Allyn | A61B 1/0676 |
| | | | 600/109 |
| 2015/0350639 A1 * | 12/2015 | Maule | G06F 3/0481 |
| | | | 348/187 |
| 2016/0000517 A1 * | 1/2016 | Kehat | A61B 34/25 |
| | | | 600/424 |

FOREIGN PATENT DOCUMENTS

| | | |
|---|---|---|
| JP | 7-194598 A | 8/1995 |
| JP | 7-306930 A | 11/1995 |
| JP | 2001-167272 A | 6/2001 |
| JP | 2005-52635 A | 3/2005 |
| JP | 2007-282794 A | 11/2007 |
| JP | 2010-35637 A | 2/2010 |
| JP | 2014-6481 A | 1/2014 |
| JP | 2015-25965 A | 2/2015 |
| JP | 2015025965 A * | 2/2015 |

* cited by examiner

ENDOSCOPE DEVICE AND METHOD FOR CONTROLLING DISPLAY CHANGE IN ENDOSCOPE DEVICE

CROSS-REFERENCE TO RELATED APPLICATIONS

This application is a continuation application of PCT International Application No. PCT/JP2016/072006, filed on Jul. 27, 2016, claiming priority based on Japanese Patent Application No. 2015-173966, filed Sep. 3, 2015, the entire contents of each of which are incorporated in this specification by reference.

BACKGROUND

Technical Field

The present invention relates to an endoscope device and a method for controlling a display change in the endoscope device.

Background Art

In the related art, there is an endoscope device that includes an insertion portion that is inserted into an imaging target so as to capture an image of a subject and a display unit on which a captured image is displayed.

In addition, as disclosed in JP-A-2014-6481, a user interface of an information processing device, on which an approximate display position is adjusted on a map through a drag operation performed on a touch panel, and a user position is finely adjusted on the map through a slide operation of vertical-axis and horizontal-axis sliders which are images for operations, is proposed.

However, in a case where the user interface of the related art is applied to an endoscope device, an endoscopic image is reduced by a display area of the image for operations of the vertical-axis and horizontal-axis sliders or the like, and an angle of view of the endoscopic image is reduced.

In addition, in a case where the user interface of the related art is applied to a portable endoscope device including a small display unit, the image for operations which is displayed on the display unit is small with respect to a size of a finger, and thus it is difficult to perform operation with a finger.

An object of the present invention is to provide an endoscope device and a method for controlling a display change in the endoscope device that includes a display unit on which a plurality of image regions that display at least one endoscopic image are arranged, enables an instruction input to be performed on an instruction input unit through a predetermined operation method corresponding to an image region, and enables display change control of the image region to be performed in response to the instruction input.

SUMMARY

There is provided an endoscope device comprising: a display configured to display a first image region and a second image region; and a controller configured to: perform first display change control to control the display to change a display state of the first image region based on an instruction input to an instruction input device through a first operation method; and perform second display change control to control the display to change a display state of the second image region based on an instruction input to the instruction input device through a second operation method.

There is provided a method comprising: arranging a first image region and a second image region on a display of an endoscope device; and performing first display change control to control the display to change a display state of the first image region based on an instruction input to an instruction input device through a first operation method; and perform second display change control to control the display to change a display state of the second image region based on an instruction input to the instruction input device through a second operation method.

There is provided a computer-readable storage device storing instructions that cause a computer to perform at least: arranging a first image region and a second image region on a display of an endoscope device; and performing first display change control to control the display to change a display state of the first image region based on an instruction input to an instruction input device through a first operation method; and perform second display change control to control the display to change a display state of the second image region based on an instruction input to the instruction input device through a second operation method.

DETAILED DESCRIPTION

Hereinafter, embodiments of the present invention will be described with reference to the figures.

First Embodiment (Configuration)

Figure 1:
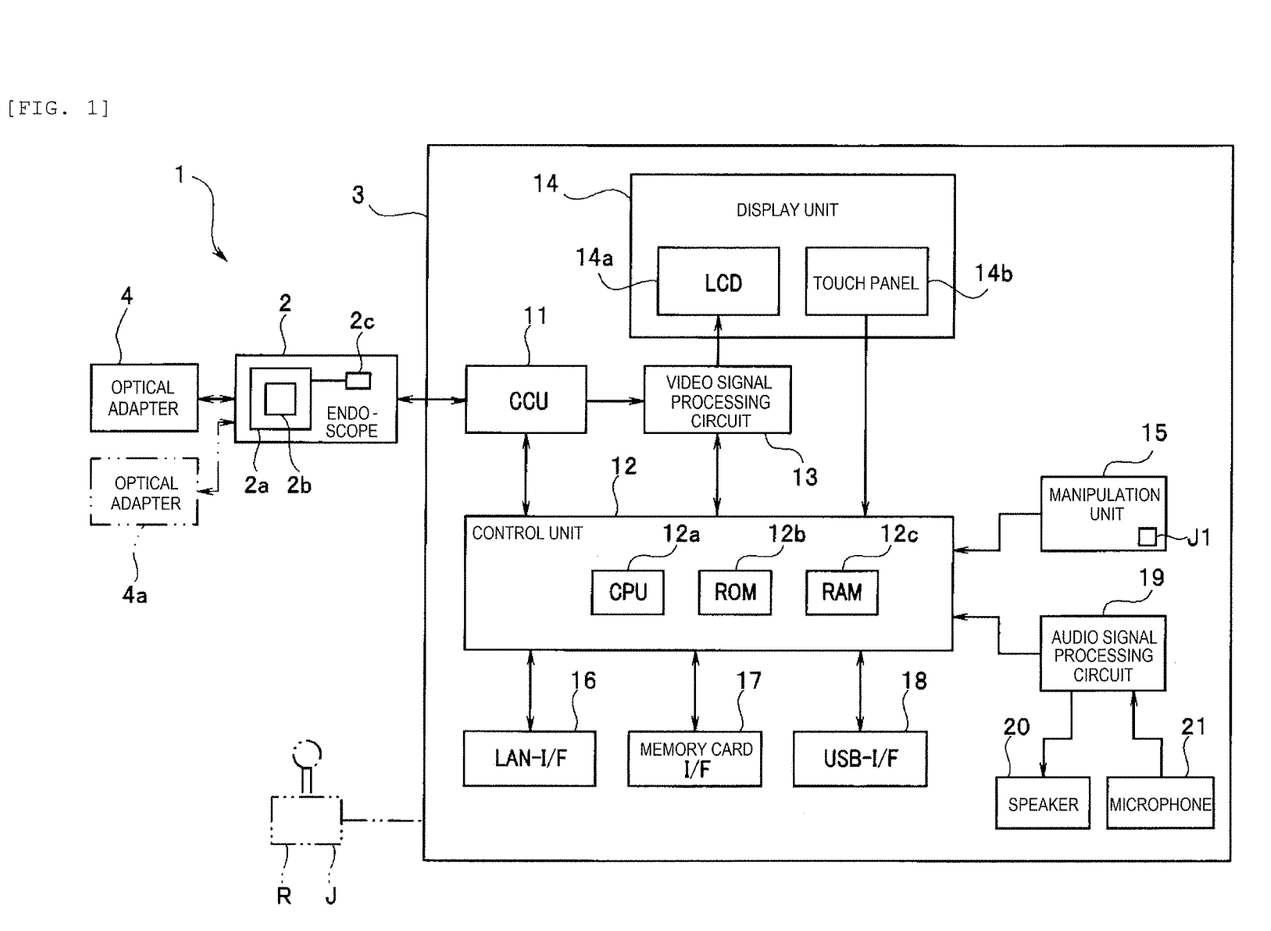
FIG. 1 is a block diagram illustrating a configuration of an endoscope device according to a first embodiment of the present invention.

FIG. 1 is a block diagram illustrating a configuration of an endoscope device 1 according to a first embodiment of the present invention.

The endoscope device 1 is configured to include an endoscope 2 as an imaging unit and a device main body 3 to which the endoscope 2 is connected. The endoscope 2 is configured to be attachable to and detachable from the device main body 3. The endoscope 2 as the imaging unit captures an image of a subject through an observation window (not illustrated) provided at a front end of an insertion portion 2a and is capable of outputting an imaging signal to the device main body 3.

The endoscope 2 is configured to have the insertion portion 2a that is capable of performing pan/tilt motion. In other words, the insertion portion 2a has a bending portion 2b that is freely bendable. The bending portion 2b is connected to an actuator 2c. The actuator 2c is connected to a control unit 12 of the device main body 3 which will be described below. When the actuator 2c receives a control signal from the control unit 12, the actuator 2c causes the bending portion 2b to perform bending motion such that the insertion portion 2a can motion in a pan direction or a tilt direction.

The insertion portion 2a is provided with an optical adapter 4 having the observation window that is attached to the front end thereof.

The device main body 3 is configured to include a camera control unit (hereinafter, referred to as a CCU) 11, a control unit 12, a video signal processing circuit 13, a display unit 14 to which a touch panel 14b is attached (hereinafter, abbreviated to a display unit), a manipulation unit 15, a LAN interface (hereinafter, abbreviated to a LAN-I/F) 16, a memory card interface (hereinafter, abbreviated to a memory card I/F) 17, a USB interface (hereinafter, abbreviated to a USB-I/F) 18, an audio signal processing circuit 19, a speaker 20, and a microphone 21.

The CCU 11 drives an imaging device (not illustrated) of the endoscope 2 under control of the control unit 12, receives an imaging signal output from the imaging device, and outputs the received signal to the video signal processing circuit 13.

The control unit 12 receives signals from various types of circuits in the device main body 3 and outputs control signals to the various types of circuits. The control unit 12 is configured to include a central processing unit (hereinafter, referred to as a CPU) 12a, a ROM 12b, and a RAM 12c.

The ROM 12b stores a measurement processing program and various types of programs of comparative observation processing or the like, and various types of setting data. The various types of setting data also include cursor moving amounts da and db which will be described below.

The cursor moving amount da is an amount corresponding to a unit moving distance of a finger on a touch panel 14b in a drag operation (operation of touching the touch panel 14b with a finger and sliding on the touch panel 14b with the finger) which will be described below. In other words, the cursor moving amount da is defined as a function of a moving distance of a finger on the touch panel 14b.

The cursor moving amount db is an amount corresponding to the number of times of taps in a tap operation (operation of touching the touch panel 14b with a finger and separating the finger from the touch panel 14b) which will be described below. In other words, the cursor moving amount db is defined as a function of the number of times of taps on the touch panel 14b with the finger.

The control unit 12 causes the zoom image region 111 to move as first display change control for changing a display state with respect to a measurement image region 101 as a first image region which will be described below, based on an instruction input when an instruction is input to the touch panel 14b as an instruction input unit through the drag operation as a first operation method, and causes the cursor 112 to move as second display change control for changing the display state with respect to the zoom image region 111 as the second image region based on an instruction input when an instruction is input to the touch panel 14b as the instruction input unit through the tap operation as a second operation method.

In addition, the control unit 12 can determine whether or not the optical adapter 4 is installed at the front end of the insertion portion 2a of the endoscope 2, based on a conduction state signal at a contact point with the optical adapter 4 via the endoscope 2.

The video signal processing circuit 13 is capable of processing an imaging signal from the CCU 11, generating an endoscopic image T, and outputting the image to the display unit 14. The video signal processing circuit 13 executes image processing suitable for various types of functions under the control of the control unit 12. For example, when a measurement function is executed, the video signal processing circuit 13 generates an image signal by superimposing the zoom image region 111 on the measurement image region 101 which will be described below, and outputs the signal to the display unit 14.

The display unit 14 includes a liquid crystal display (hereinafter, referred to as an "LCD") 14a and a touch panel 14b as the instruction input unit.

On the LCD 14a of the display unit 14, the measurement image region 101 as the first image region and the zoom image region 111 as the second image region are arranged. On the LCD 14a, the zoom image region 111 as the second image region can be superimposed on the measurement image region 101 as the first image region. On the LCD 14a, it is possible to arrange the zoom image region 111 by transmitting through the measurement image region 101. Note that, on the LCD 14a, the measurement image region 101 and the zoom image region 111 can be arranged at positions adjacent to each other.

The touch panel 14b as the instruction input unit is an electrostatic type touch panel 14b and is provided to be in close contact with the LCD 14a on a display screen. A positional signal from the touch panel 14b through a touch operation with a finger is output to the control unit 12.

It is possible to perform the instruction input to the touch panel 14b as the instruction input unit through the drag operation as the first operation method and the tap operation as the second operation method.

The drag operation as the first operation method is an operation method in which a distance from an operation start position to an operation end position on the touch panel 14b is equal to or longer than a predetermined distance. The tap operation as the second operation method is an operation method in which a distance from an operation start position to an operation end position on the touch panel 14b is shorter than the predetermined distance. The predetermined distance is set in advance to a distance with which it is possible to discriminate between the drag operation and the tap operation.

The manipulation unit 15 includes a plurality of operating elements such as a freeze button, a release button, a joystick, a zoom operation button, or a menu button.

The LAN-I/F 16 is an interface for connecting to a local area network (hereinafter, referred to as a LAN). The endoscope device 1 is capable of communicating with an external device connected to the LAN via the LAN-I/F 16.

The memory card I/F 17 is an interface for installing a memory card as a storage medium. The endoscope device 1 is capable of reading or writing various types of data of the endoscopic image T or the like from or to the memory card via the memory card I/F 17.

The USB-I/F 18 is an interface for connecting with a universal serial bus (USB) cable or a USB device. The endoscope device 1 is capable of reading or writing various types of data of the endoscopic image T or the like from or to the USB device via the USB-I/F 18.

The audio signal processing circuit 19 processes, under the control of the control unit 12, an audio signal from the control unit 12, and outputs an audio sound from the speaker 20. In addition, the audio signal processing circuit processes an audio signal from a microphone 21 and outputs the signal to the control unit 12. The endoscope device 1 is capable of recording various types of images and audio sounds and replaying the images and sounds.

A user as a medical examiner can operate the touch panel 14b or the manipulation unit 15, thereby executing various types of functions of the endoscope device 1. The control unit 12 is capable of reading a predetermined program from the ROM 12b in response to a command instructed through the touch panel 14b or the manipulation unit 15, executing the program while using the RAM 12c as a working region, thereby arranging the measurement image region 101 and the zoom image region 111 on the LCD 14a, and displaying the endoscopic image T thereon or recording the obtained endoscopic image T to the memory card. Further, the user selects a desired command from a menu screen displayed on a screen of the LCD 14a and instructs execution, and thereby the user can cause the endoscope device 1 to execute a measurement function or a comparative observation function.

(Configuration of Image)

Next, a configuration of an image displayed on the display unit 14 during the execution of the measurement function will be described.

Figure 2:
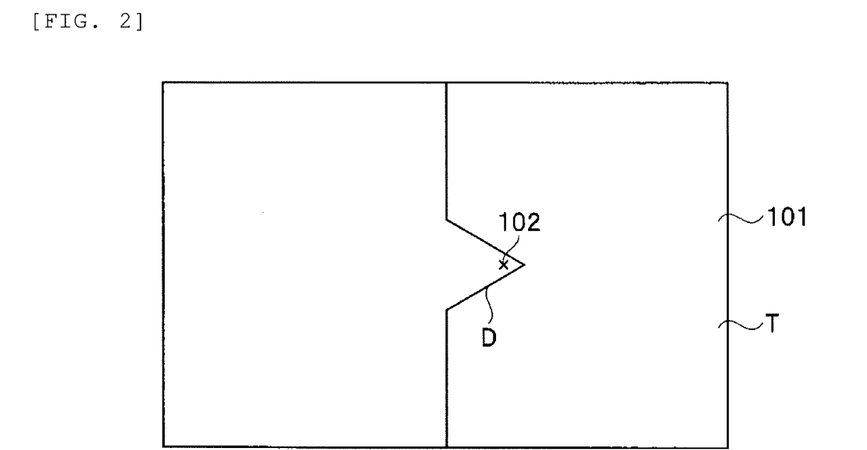
FIG. 2 is a diagram illustrating an example of a measurement image region in the endoscope device according to the first embodiment of the present invention.
Figure 3:
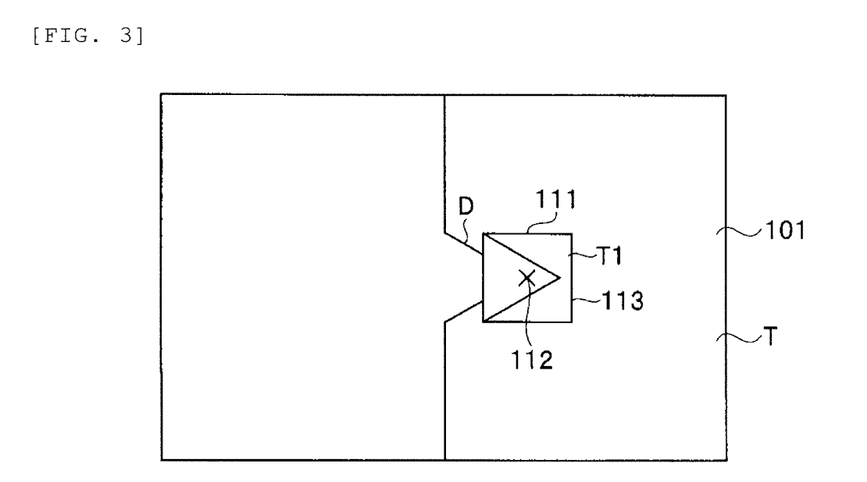
FIG. 3 is a diagram illustrating an example in which a zoom image region is displayed by being superimposed on the measurement image region in the endoscope device according to the first embodiment of the present invention.

FIG. 2 is a diagram illustrating an example of the measurement image region 101 in the endoscope device 1 according to the first embodiment of the present invention. FIG. 3 is a diagram illustrating an example in which the zoom image region 111 is superimposed on the measurement image region 101 in the endoscope device 1 according to the first embodiment of the present invention.

FIGS. 2 and 3 illustrate an example of a graphical user interface (hereinafter, referred to as a "GUI") that is displayed on the display unit 14.

FIG. 2 illustrates, as the endoscopic image T, a part of a turbine blade of a jet engine having a chip D.

As illustrated in FIG. 2, the measurement image region 101 as the first image region is a region for displaying the endoscopic image T that is obtained through imaging by the endoscope 2, and is configured to have a cursor 102 for designating a measurement point on the endoscopic image T.

In the state in which the measurement image region 101 in FIG. 2 is displayed, the zoom image region 111 illustrated in FIG. 3 is displayed when the user touches a zoom button not illustrated.

The zoom image region 111 as the second image region is a region that is configured to have the cursor 112 for designating the measurement point and a small rectangular frame 113 having a partially enlarged image T1 of the endoscopic image T and that is superimposed on a part of the measurement image region 101 as the first image region. The cursor 112 of the zoom image region 111 is displayed at the same position as the cursor 102 such that the cursor 102 of the measurement image region 101 is hidden. The zoom image region 111 has the small rectangular frame 113 in which the partially enlarged image T1 of the endoscopic image T that is obtained by enlarging a region containing the cursor 102 by a predetermined magnification is displayed. For example, the predetermined magnification is any magnification in a range of twice to ten times. Note that the predetermined magnification may be set by a zoom button not illustrated.

The cursor 102 of the measurement image region 101 or the cursor 112 of the zoom image region 111 is configured to be able to designate the measurement point. Designation of two measurement points enables the endoscope device 1 to measure a distance between the measurement points.

(Operation)

Next, an operation of the endoscope device 1 of the first embodiment will be described.

Figure 4:
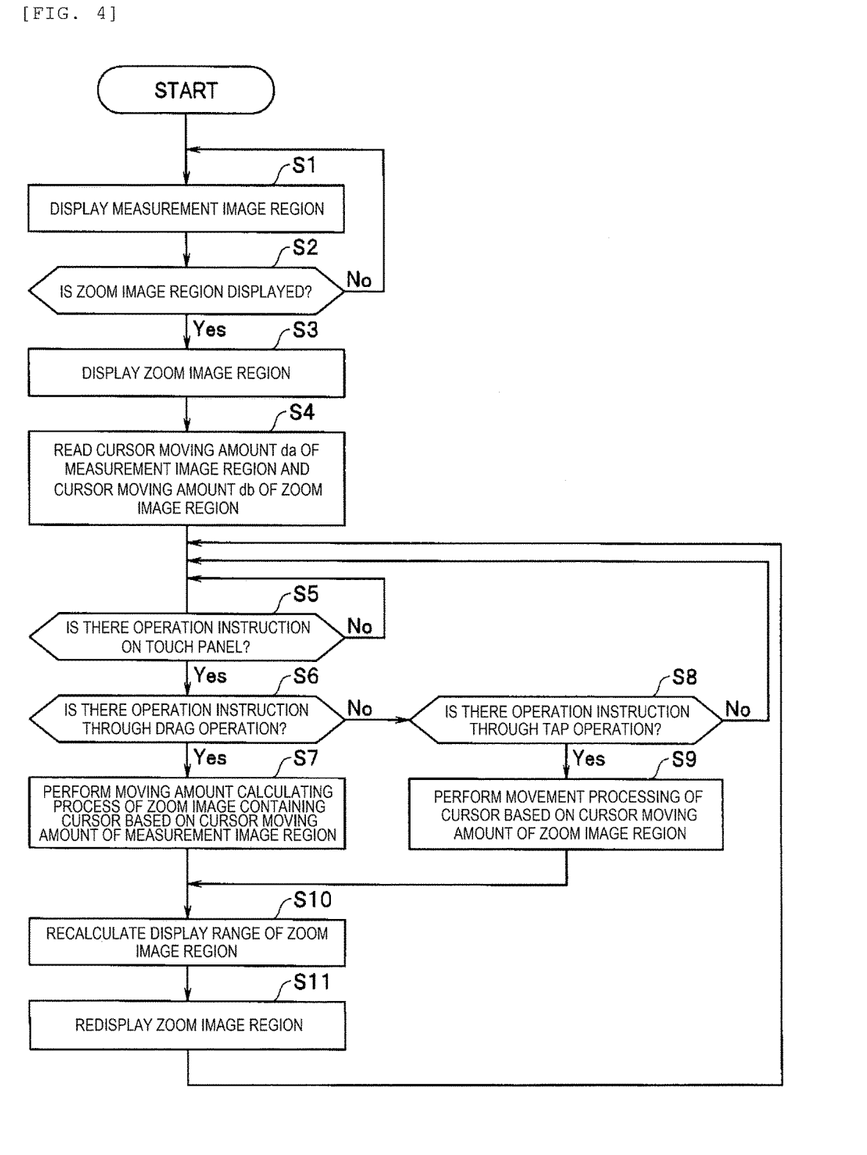
FIG. 4 is a flowchart illustrating an example of flow of measurement processing used in the measurement image region and the zoom image region in the endoscope device according to the first embodiment of the present invention.
Figure 5:
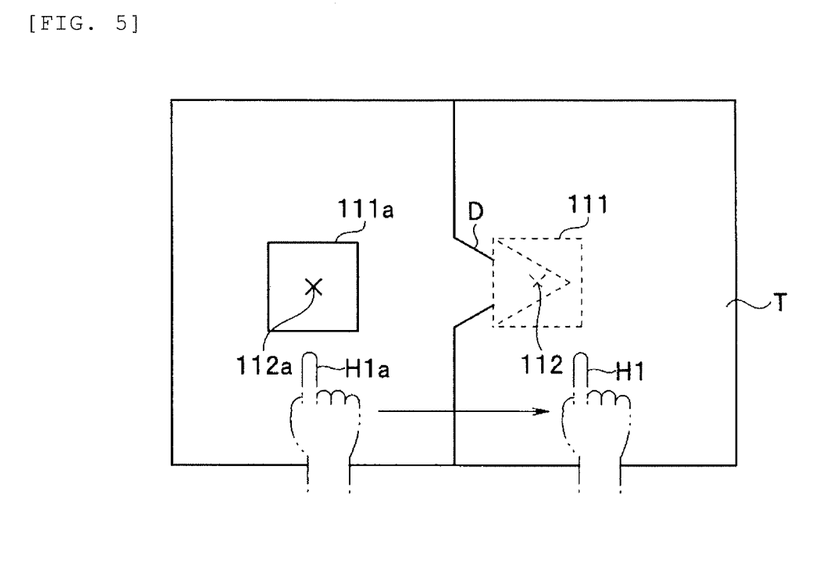
FIG. 5 is a diagram illustrating a drag operation in the endoscope device according to the first embodiment of the present invention.
Figure 6:
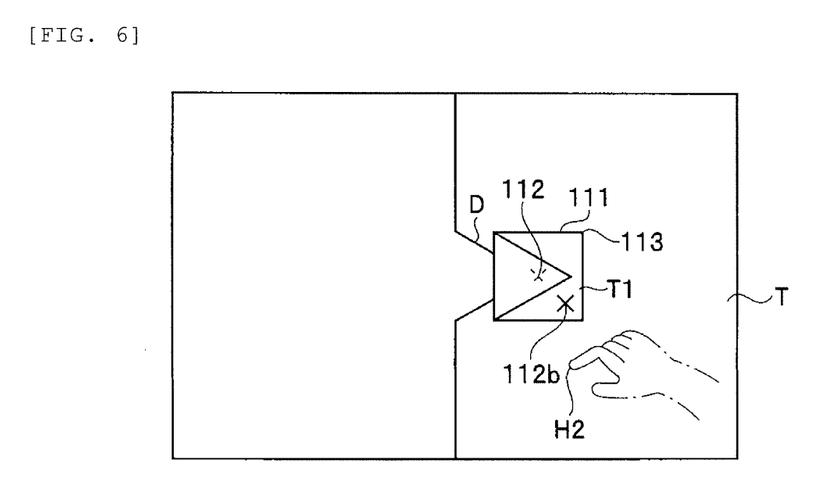
FIG. 6 is a diagram illustrating a tap operation in the endoscope device according to the first embodiment of the present invention.
Figure 7:
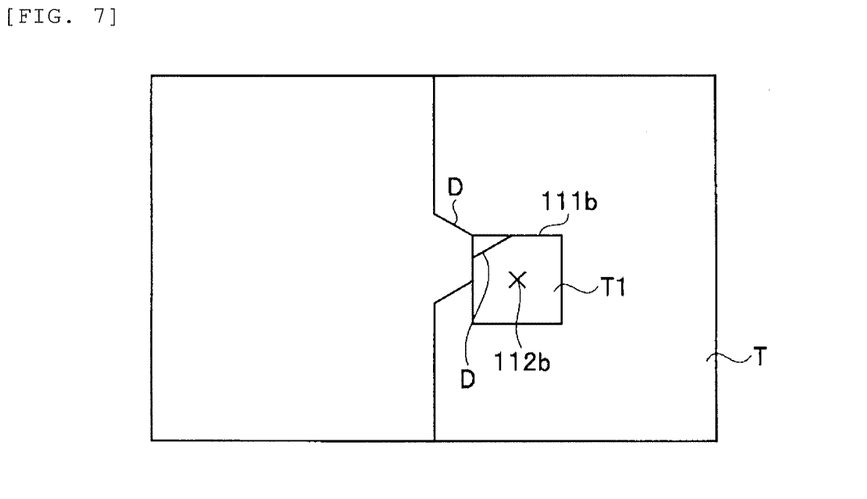
FIG. 7 is a diagram illustrating an example of a state in which the zoom image region is caused to move in the endoscope device according to the first embodiment of the present invention.

FIG. 4 is a flowchart illustrating an example of flow of measurement processing used in the measurement image region 101 and the zoom image region 111 in the endoscope device 1 according to the first embodiment of the present invention. FIG. 5 is a diagram illustrating the drag operation in the endoscope device 1 according to the first embodiment of the present invention. In FIG. 5, a zoom image region 111a and a cursor 112a before movement are represented by a solid line, and the zoom image region 111 and the cursor 112 which are not displayed after movement are represented by a dashed line. FIG. 6 is a diagram illustrating the tap operation in the endoscope device 1 according to the first embodiment of the present invention. FIG. 7 is a diagram illustrating an example of a state in which the zoom image region 111 is caused to move in the endoscope device 1 according to the first embodiment of the present invention.

When an instruction of a measurement processing start is input from the manipulation unit 15 or the touch panel 14b, the CPU 12a of the control unit 12 reads and executes a measurement processing program from the ROM 12b, and thereby the measurement processing in FIG. 4 is performed.

The control unit 12 displays the measurement image region 101 (Step (hereinafter, abbreviated to "S") 1). The control unit 12 transmits a control signal to the video signal processing circuit 13. The video signal processing circuit 13 generates the endoscopic image T from an imaging signal that is transmitted from the CCU 11, and displays the measurement image region 101 (for example, the measurement image region 101 in FIG. 2) including the endoscopic image T to the display unit 14.

The control unit 12 determines whether or not the zoom image region 111 is displayed (S2). In S2, whether or not a zoom button (not illustrated) is subjected to a touch operation is determined. When the zoom button is touched (S2: YES), the process proceeds to S3. Conversely, when the zoom button is not touched (S2: NO), the process returns to S1. In other words, until the zoom button is touched, the processes of S1 and S2 are repeatedly performed. Note that description is omitted in FIG. 4; however, the user can move the cursor of the measurement image region 101 through the drag operation while the process of S2 is repeatedly performed. Note that an instruction of display of the zoom image region 111 can be input through the zoom button, and an instruction of input of a predetermined magnification may be input through the zoom button.

The control unit 12 displays the zoom image region 111 (S3). In S3, the control unit 12 transmits the control signal to the video signal processing circuit 13. The video signal processing circuit 13 generates the zoom image region 111, superimposes the zoom image region 111 on the measurement image region 101, and causes the regions to be displayed on the display unit 14.

The control unit 12 reads the cursor moving amount da of the measurement image region 101 and the cursor moving amount db of the zoom image region 111 from the ROM 12b (S4).

The control unit 12 determines whether or not there is an operation instruction (S5). When there is an operation instruction (S5: YES), the process proceeds to S6. Conversely, when there is no operation instruction (S5: NO), the process returns to S5. In other words, until there is an operation instruction on the touch panel 14b, the process of S5 is repeatedly performed.

The control unit 12 determines whether or not the operation instruction is an operation instruction through the drag operation (S6). In S6, the control unit determines whether or not the operation instruction in S5 is an operation instruction through the drag operation, and, when the operation instruction is obtained through the drag operation (S6: YES), the process proceeds to S7. Conversely, when the operation instruction is not obtained through the drag operation (S6: NO), the process proceeds to S8.

The control unit 12 performs movement operation processing of the zoom image region 111 containing the cursor 112, based on the cursor moving amount of the measurement image region 101 (S7). In S7, the zoom image region 111 is not displayed, and the movement operation processing of the zoom image region 111 containing the cursor 112 is performed in a direction indicated by the drag operation by a distance depending on the cursor moving amount da.

The direction indicated by the drag operation is a direction that is determined by a difference between a position on the touch panel 14b at which a finger H1a performs touching and a position at which a finger H1 is separated from the touch panel after the finger slides thereon.

The distance depending on the cursor moving amount da is a distance that is determined by a difference between the position on the touch panel 14b at which the finger H1a performs touching and the position at which the finger H1 is separated from the touch panel after the finger H1 slides thereon.

For example, as illustrated in FIG. 5, when the cursor moving amount da per the movement of 1 cm of the finger on the touch panel 14b is set to 1 cm, a user touches a lower side of the zoom image region 111a by the finger H1a, the finger slides by 5 cm in a rightward direction as illustrated by the finger H1, and the finger H1 is separated from the touch panel 14b, the zoom image region 111a and the cursor 112a are not displayed along with the start of the drag operation, and the movement operation processing is performed by 5 cm in the rightward direction along with the end of the drag operation while the zoom image region and the cursor are not displayed as shown by the zoom image region 111 and the cursor 112 represented by the dashed line in FIG. 5.

When the process of S7 is ended, the process proceeds to S10.

When the operation instruction in S6 is not the operation instruction through the drag operation, the control unit 12 determines whether or not the operation instruction is the operation instruction through the tap operation (S8). When the operation instruction is the operation instruction through the tap operation (S8: YES), the process proceeds to S9. Conversely, when the operation instruction is not the operation instruction through the tap operation (S8: NO), the process returns to S5. In other words, when the operation instruction on the touch panel 14b in S5 is not the operation instruction through any of the drag operation or the tap operation, the process returns to S5.

As illustrated in FIG. 7, the control unit 12 performs cursor movement processing, based on the cursor moving amount of the zoom image region 111 (S9). In S9, the cursor is caused to move in a direction instructed by the tap operation by a distance depending on the cursor moving amount db.

The direction instructed by the tap operation is a direction from a position of the cursor 112 to a position tapped by a finger H2 on the touch panel 14b.

The distance depending on the cursor moving amount db is a distance that is determined by multiplying the number of times of taps on the touch panel 14b by the finger H2 by the cursor moving amount db.

For example, as illustrated in FIG. 6, when the cursor moving amount db per tap is set to 0.1 cm, and the user taps by the finger H2 five times on an obliquely right lower side of the cursor 112, the cursor 112 moves in a right lower direction by 0.5 cm as shown by the cursor 112b in FIG. 6.

When the process of S9 is ended, the process proceeds to S10.

The control unit 12 recalculates a display range of the zoom image region 111 (S10). In S10, the display range of the enlarged image displayed in the zoom image region 111 is recalculated by using the position of the cursor 112b after the movement and the predetermined magnification.

The control unit 12 redisplays the zoom image region 111 (S11). When the zoom image region 111 moves in S7, or when the position of the cursor 112b after the movement in S9 is separated from the center of the zoom image region 111 by a distance equal to or longer than a predetermined distance, the control unit 12 redisplays the zoom image region 111b at the position of the cursor 112b. Specifically, the control unit 12 transmits information of the display range recalculated in S10 to the video signal processing circuit 13. The video signal processing circuit 13 redisplays the zoom image region 111b on the display unit 14 based on the information of the recalculated display range. Note that, when the position of the cursor 112b after movement in S9 is not separated from the center of the zoom image region 111 by a distance equal to or longer than the predetermined distance, the zoom image region 111b is not redisplayed.

For example, the predetermined distance is half of a distance from the center of the zoom image region 111 to an outer edge. Note that the zoom image region 111a is not subjected to non-display in the drag operation, but the zoom image region may be displayed while being sequentially updated.

After the zoom image region 111b is redisplayed, the process returns to S5, and standby for the following operation instruction is performed.

The processes from S1 to S11 configure the measurement processing.

According to the first embodiment described above, it is possible to provide the endoscope device 1 and a method for controlling the display change in the endoscope device 1 that includes the display unit 14 on which the measurement image region 101 and the zoom image region 111 are arranged, in which it is possible to perform the instruction input with respect to the measurement image region 101 through the drag operation, it is possible to perform the instruction input with respect to the zoom image region 111 through the tap operation, and it is possible to perform display change control of the image region depending on the instruction input.

Modification Example of First Embodiment

In the first embodiment, the display unit 14 has the measurement image region 101 and the zoom image region 111 which are superimposed; however, on the display unit 14, a left image region L1 and a right image region R1 which can be arranged in stereo display, may be arranged at positions adjacent to each other or both of the measurement image region 101 and the zoom image region 111 having disparity from each other may be arranged to each of the left image region L1 and the right image region R1.

Figure 8:
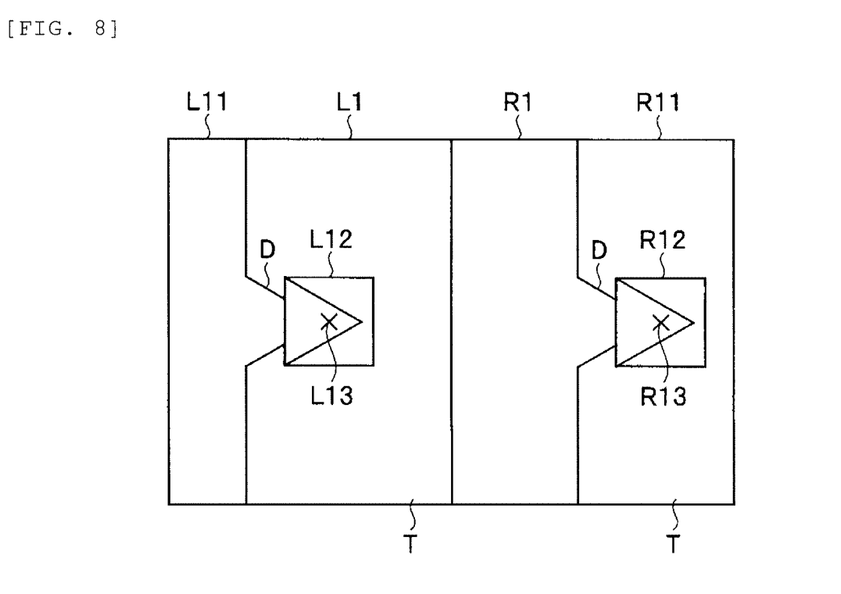
FIG. 8 is a diagram illustrating an example of stereo measurement processing in an endoscope device according to a modification example of the first embodiment of the present invention.

FIG. 8 is a diagram illustrating an example of stereo measurement processing in the endoscope device 1 according to a modification example of the first embodiment of the present invention. Description of the same configuration or operation as that of the first embodiment is omitted.

The endoscope 2 is provided with the optical adapter 4a for the stereo measurement that is attached to the front end thereof. The optical adapter 4a has two observation windows, and is configured to provide two optical images of a subject that have the disparity from each other on an imaging surface of an imaging device of the insertion portion 2a of the endoscope 2. In this manner, the endoscope 2 is capable of displaying a stereo image for the stereo measurement on the display unit 14.

The stereo image is configured to have the left image region L1 and the right image region R1.

On the left image region L1, a left-eye target measurement image region L11 and a left-eye target zoom image region L12 as left-eye images are displayed. On the right image region R1, a right-eye target measurement image region R11 and a right-eye target zoom image region R12 as right-eye images are displayed. The left-eye image and the right-eye image are configure to have the disparity from each other.

The left-eye target zoom image region L12 can be caused to move through the drag operation of the left image region L1. A cursor L13 of the left-eye target zoom image region L12 can be caused to move through the tap operation of the left image region L1. The right-eye target zoom image region R12 can be caused to move through the drag operation of the right image region R1. A cursor R13 of the right-eye target zoom image region R12 can be caused to move through the tap operation of the right image region R1.

When the left-eye target zoom image region L12 or the cursor L13 of the left image region L1 moves, the control unit 12 calculates a position of the right-eye target zoom image region R12 or the cursor R13 of the right image region R1 depending on the disparity, and causes the right-eye target zoom image region R12 or the cursor R13 to move. When the right-eye target zoom image region R12 or the cursor R13 of the right image region R1 moves, similarly, the control unit 12 causes the left-eye target zoom image region L12 or the cursor L13 of the left image region L1 to move.

According to the modification example of the first embodiment, it is possible to provide the endoscope device 1 and a method for controlling the display change in the endoscope device 1 that includes the display unit on which the left image region L1 and the right image region R1 which can be disposed in stereo display are arranged, in which it is possible to perform the instruction input of moving of the zoom image regions L12 and R12 through the drag operation with respect to the measurement image regions L11 and R11 of the display regions, it is possible to perform the instruction input of moving of the cursors L13 and R13 through the tap operation with respect to the zoom image regions L12 and R12 of the display regions, and it is possible to perform display change control of the image region depending on the instruction input.

Second Embodiment

In the first embodiment and the modification example of the first embodiment, an example in which the present invention is applied to the measurement processing using the measurement image region 101 and the zoom image region 111 is described; however, the present invention is also applied to the comparative observation processing using alive image region 201 and a replay image region 211.

Figure 9:
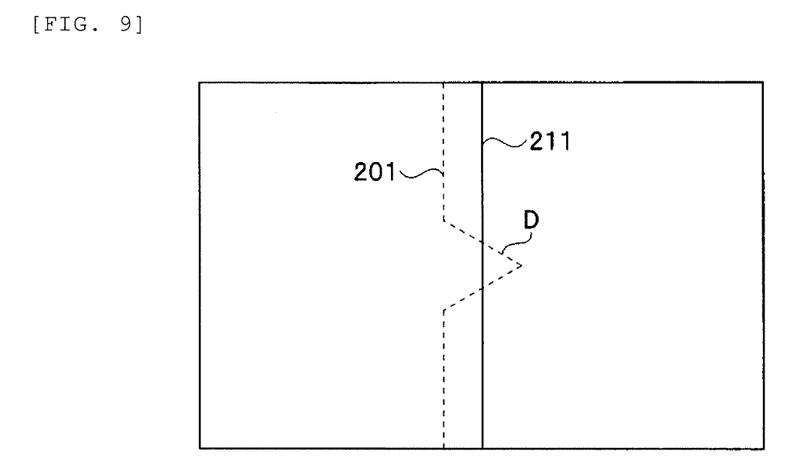
FIG. 9 is a diagram illustrating an example of comparative observation processing in an endoscope device according to a second embodiment of the present invention.

FIG. 9 is a diagram illustrating an example of the comparative observation processing in the endoscope device 1 according to a second embodiment of the present invention. Description of the same configuration or operation in the first embodiment and the modification example of the first embodiment is omitted.

In the second embodiment, on the display unit 14, the live image region 201 (dashed line in FIG. 9) as the first image region for displaying the endoscopic image T is disposed and the replay image region 211 (solid line in FIG. 9) as the second image region for displaying a replay image of the endoscopic image T is disposed to be superimposed on the live image region 201. The replay image region 211 is displayed by transmitting through the live image region 201 at a predetermined transmittance. For example, the predetermined transmittance is 50%.

The display change control with respect to the live image region 201 as the first image region is performed by causing the insertion portion 2a to pan and tilt by the drag operation as the first operation method, and the display change control of causing the replay image region 211 to move in a pan direction or in a tilt direction is performed through the tap operation as the second operation method with respect to the replay image region 211 as the second image region.

In FIG. 9, the live image region 201 of a turbine blade having the chip D and the replay image region 211 of the turbine blade that does not have the chip are displayed in which it is possible to find the chip of the turbine blade.

Next, the operations of the second embodiment will be described.

Figure 10:
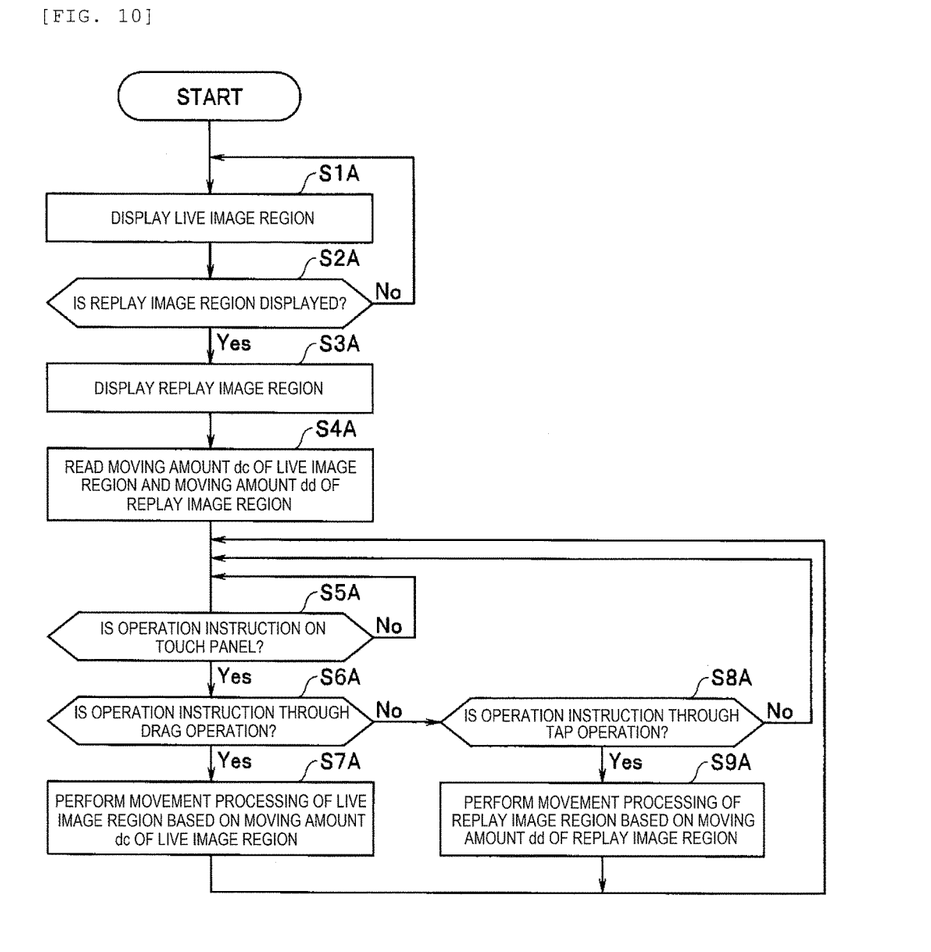
FIG. 10 is a flowchart illustrating an example of flow of comparative observation processing in the endoscope device according to the second embodiment of the present invention.

FIG. 10 is a flowchart illustrating an example of flow of the comparative observation processing in the endoscope device 1 according to the second embodiment of the present invention.

The control unit 12 displays the live image region 201 (S1A). The control unit 12 transmits a control signal to the video signal processing circuit 13. The video signal processing circuit 13 generates the endoscopic image T from an imaging signal that is transmitted from the CCU 11, and displays the live image region 201 (dashed line in FIG. 9) including the endoscopic image T to the display unit 14.

The control unit 12 determines whether or not the replay image region 211 is displayed (S2A). In S2A, whether or not an operation button (not illustrated) is subjected to a touch operation is determined. When the operation button is touched (S2A: YES), the process proceeds to S3A. Conversely, when the operation button is not touched (S2A: NO), the process returns to S1A.

The control unit 12 displays the replay image region 211 (S3A). The control unit 12 reads a replay image recorded in the ROM 12b or the memory card (not illustrated) and outputs the replay image to the video signal processing circuit 13. The video signal processing circuit 13 superimposes the replay image region 211 containing the replay image on the live image region 201, and causes the regions to be displayed on the display unit 14 as illustrated in FIG. 9.

The control unit 12 reads a moving amount dc of the live image region 201 and a moving amount dd of the replay image region 211 from the ROM 12b (S4A).

The moving amount dc of the live image region 201 is a distance depending on a unit moving distance of a finger on the touch panel 14b through the drag operation. In other words, the moving amount dc is defined as a function of a moving distance of a finger on the touch panel 14b.

The moving amount dd of the replay image region 211 is a distance depending on the number of times of taps in the tap operation. In other words, the moving amount dd is defined as a function of the number of times of taps on the touch panel 14b with the finger.

The control unit 12 determines whether or not there is an operation instruction on the touch panel 14b (S5A). When there is an operation instruction (S5A: YES), the process proceeds to S6A. Conversely, when there is no operation instruction (S5A: NO), the process returns to S5A.

The control unit 12 determines whether or not the operation instruction is an operation instruction through the drag operation (S6A). In S6A, the control unit determines whether or not the operation instruction in S5A is an operation instruction through the drag operation, and, when the operation instruction is obtained through the drag operation (S6A: YES), the process proceeds to S7A. Conversely, when the operation instruction is not obtained through the drag operation (S6A: NO), the process proceeds to S8A.

The control unit 12 performs movement processing of the live image region 201, based on the moving amount dc of the live image region 201 (S7A). In S7A, the live image region 201 is caused to move in a direction instructed by the drag operation by a distance depending on the moving amount dc.

Specifically, the control unit 12 transmits the control signal to the actuator 2c, causes the insertion portion 2a to perform the pan/tilt motion, and causes the live image region 201 to be subjected to scroll movement in the direction instructed through the drag operation by a distance depending on the moving amount dc.

When the process of S7A is ended, the process proceeds to S10A.

When the operation instruction in S6A is not the operation instruction through the drag operation, the control unit 12 determines whether or not the operation instruction is the operation instruction through the tap operation (S8A). When the operation instruction is the operation instruction through the tap operation (S8A: YES), the process proceeds to S9A. Conversely, when the operation instruction is not the operation instruction through the tap operation (S8A: NO), the process returns to S5A.

The control unit 12 performs cursor movement processing, based on the cursor moving amount of the replay image region 211 (S9A). In S9A, the cursor is caused to move in a direction instructed by the tap operation by a distance depending on the cursor moving amount dd.

Specifically, the control unit 12 transmits, to the video signal processing circuit 13, the control signal for causing the replay image region 211 to be subjected to the scroll movement in the direction instructed through the tap operation by a distance depending on the moving amount dd. The video signal processing circuit 13 generates the replay image region 211 subjected to the scroll movement, based on the control signal from the control unit 12, and displays the region on the LCD 14a.

The direction instructed through the tap operation is a direction determined by a difference between the center of the replay image region 211 and the position at which the tap operation is performed.

When the process of S9A is ended, the process returns to S5A, and standby for the following operation instruction is performed.

The processes from S1A to S9A configure the comparative observation processing.

According to the second embodiment described above, it is possible to provide the endoscope device 1 and a method for controlling the display change in the endoscope device 1 in which the live image region 201 and the replay image region 211 are superimposed, it is possible to perform the instruction input with respect to the live image region 201 through the drag operation, it is possible to perform the instruction input with respect to the replay image region 211 through the tap operation, and it is possible to perform display change control of the image region depending on the instruction input.

Modification Example 1 of Second Embodiment

According to the second embodiment, when the live image region 201 or the replay image region 211 is subjected to the scroll movement, an image and a moving direction of a control target are not displayed; however, the image and the moving direction of the control target may be displayed.

Figure 11:
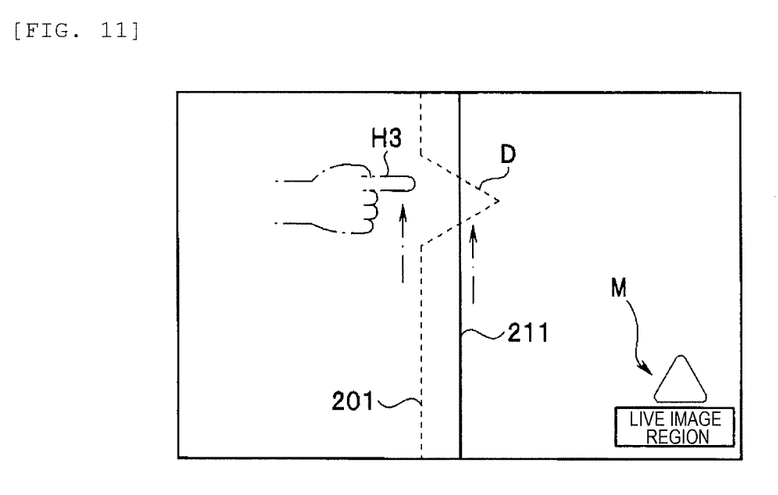
FIG. 11 is a diagram illustrating an example in which a movement display image for displaying a control target image region and a moving direction is displayed in the endoscope device according to Modification Example 1 of the second embodiment of the present invention.

FIG. 11 is a diagram illustrating an example in which a movement display image M for displaying a control target image region and a moving direction is displayed in the endoscope device 1 according to Modification Example 1 of the second embodiment of the present invention.

According to Modification Example 1 of the second embodiment, when the control unit 12 performs the display change control with respect to the live image region 201 as the first image region, the control unit 12 causes the display unit 14 to display that a target of the display change control is the live image region 201, and a moving direction of the live image region 201. Further, when the control unit 12 performs the display change control with respect to the replay image region 211 as the second image region, the control unit 12 causes the display unit 14 to display that a target of the display change control is the replay image region 211, and a moving direction of the replay image region 211.

Specifically, when the user inputs an instruction of causing any of the live image region 201 or the replay image region 211 to move with respect to the touch panel 14b, the movement display image M is displayed in a right lower portion of the LCD 14a.

For example, the movement display image M is configured to include a triangle, an arrow, or the like that indicates moving directions of the live image region 201 or the replay image region 211.

The movement display image M is configured to include names (for example, the live image region, the replay image region, or the like) of the image regions as the movement targets.

In addition, the display may be distinguishably configured such that the triangle represents the live image region and the arrow represents the replay image region.

In FIG. 11, the user performs the drag operation upward by the finger H3, and thereby the live image region 201 is subjected to upward scroll movement, and a triangle representing upward movement of the live image region 201 as the movement display image M and characters of "live image region" as the control target below the triangle are displayed.

According to the configuration, the target of the display change control and moving direction are displayed on the LCD 14a, and the user easily knows.

Modification Example 2 of Second Embodiment

According to the second embodiment and Modification Example 1 of the second embodiment, the live image region 201 and the replay image region 211 are superimposed; however, the live image region 201 and the replay image region 211 may be arranged at positions adjacent to each other.

Figure 12:
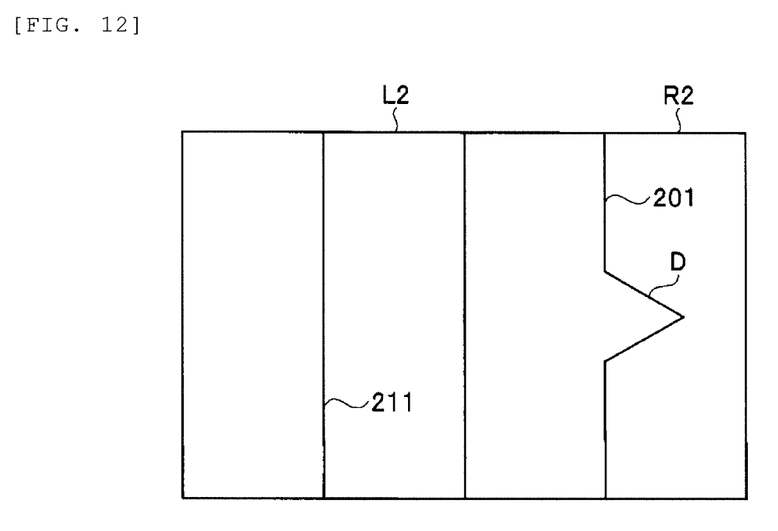
FIG. 12 is a diagram illustrating an example in which alive image region and a replay image region are arranged side by side in the endoscope device according to Modification Example 2 of the second embodiment of the present invention.

FIG. 12 is a diagram illustrating an example in which the live image region 201 and the replay image region 211 are arranged side by side in the endoscope device 1 according to Modification Example 2 of the second embodiment of the present invention.

Modification Example 2 of the second embodiment has a configuration in which the live image region 201 and the replay image region 211 are displayed at positions adjacent to each other. In FIG. 12, the live image region 201 is disposed on the right side on the LCD 14a, and the replay image region 211 is disposed on the left side on the LCD 14a. Note that, the live image region 201 and the replay image region 211 may be arranged to be opposite on the left and right sides.

The insertion portion 2a is caused to perform the pan/tilt motion through the drag operation, and thereby the live image region 201 can be subjected to the scroll movement. In addition, the replay image region 211 can be subjected to the scroll movement through the tap operation.

According to the configuration, it is possible to provide the endoscope device 1 and a method for controlling the display change in the endoscope device 1 in which the live image region 201 and the replay image region 211 are arranged at positions adjacent to each other, in which it is possible to perform the instruction input with respect to the live image region 201 through the drag operation, it is possible to perform the instruction input with respect to the replay image region 211 through the tap operation, and it is possible to perform display change control of the image region depending on the instruction input.

Modification Example 3 of Second Embodiment

According to the second embodiment, Modification Example 1 of the second embodiment, Modification Example 2 of the second embodiment, the live image region 201 and the replay image region 211 can be subjected to the operation; however, the live image region 201 and a position instruction mark image region 311 which indicates a position of damage in the subject, may be subjected to the operation.

Figure 13:
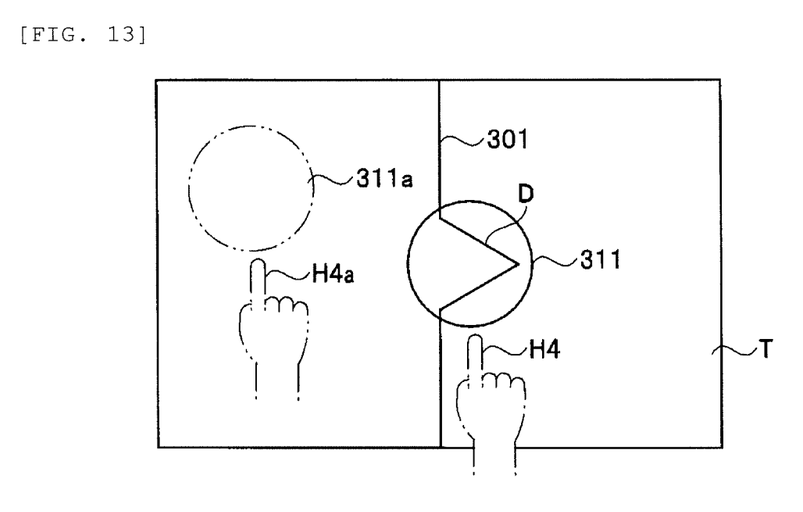
FIG. 13 is a diagram illustrating examples of a live image region and a position instruction mark image region in the endoscope device according to Modification Example 3 of the second embodiment of the present invention.

FIG. 13 is a diagram illustrating examples of the live image region 301 and the position instruction mark image region 311 in the endoscope device 1 according to Modification Example 3 of the second embodiment of the present invention.

Modification Example 3 of the second embodiment has a configuration in which the live image region 301 and the position instruction mark image region 311 are included.

The live image region 301 causes the insertion portion 2a to perform the pan/tilt motion through the drag operation on the touch panel 14b, and thereby it is possible to perform the scroll movement.

For example, the position instruction mark image region 311 is configured to have circular shape. The position instruction mark image region 311 is movable through the tap operation in a direction instructed through the tap operation by a distance depending on the moving amount dd.

The direction instructed through the tap operation is a direction determined by a difference between the center of position instruction mark image region 311 and the position of the tap operation.

The distance depending on the moving amount dd is a distance obtained by multiplying the number of times of taps by the moving amount dd.

When there is an instruction input from the user through an operation button (not illustrated) or the like, the position instruction mark image region 311 is fixed to the live image region 301. In this manner, the user can dispose the position instruction mark image region 311 at a damage position of the live image region 301.

Note that the position instruction mark image region 311 may have an annotation function of including a figure such as a text box or an arrow.

FIG. 13 illustrates the example in which the finger H4a is caused to move to the position of the finger H4 through the drag operation, and thereby the position instruction mark image region 311a is caused to move to the position of the chip D of the endoscopic image T and the position instruction mark image region 311 is fixed.

According to the configuration, a live image region 301 and the position instruction mark image region 311 are arranged, it is possible to perform the instruction input with respect to the live image region 301 through the drag operation, it is possible to perform the instruction input with respect to the position instruction mark image region 311 through the tap operation, and it is possible to perform display change control of the image region depending on the instruction input.

According to the first embodiment, the modification example of the first embodiment, second embodiment, Modification Example 1 of the second embodiment, Modification Example 2 of the second embodiment, and Modification Example 3 of the second embodiment (hereinafter, referred to as the "first embodiment) which are described above, it is possible to provide the endoscope device and a method for controlling the display change of the endoscope device in which a plurality of image regions that display at least one endoscopic image are arranged on the display unit, it is possible to perform the instruction input with respect to the instruction input unit through a predetermined operation method corresponding to an image region, and it is possible to perform the display change control of the image region in response to the instruction input.

Note that, in the first embodiment or the like, the cursor moving amounts da and dc are defined as a function of a moving distance of the finger on the touch panel 14b; however, the cursor moving amount may be defined as a function of a speed obtained when the finger is separated from the touch panel 14b. In this manner, it is possible to operate the first image region even through a flick operation (operation of sliding to bounce on the touch panel 14b with a finger) and a swipe operation (operation of sliding to sweep over the touch panel 14b with a finger), instead of the drag operation.

Note that, in the first embodiment or the like, the cursor moving amounts db and dd are defined as a function of the number of taps; however, the cursor moving amount may be defined as a function of a period of tap time (that is, a total period of time during which the touch panel 14b is touched). In this manner, it is possible to operate the second image region even through a long tap operation (operation of tapping on the touch panel 14b), instead of the tap operation.

Note that, in the first embodiment or the like, the instruction input unit is configured of the touch panel 14b; however, the instruction input unit may be configured by a joystick J represented by a two-dot chain line in FIG. 1. In this case, in the first embodiment or the like, the drag operation is replaced with an operation in which a period of tilting time per tilt of the joystick J is equal to or longer than a predetermined period of time, and the instruction input through the tap operation may be replaced with an operation in which the period of tilt time per tilt of the joystick J is shorter than the predetermined period of time. The predetermined period of time is set in advance to a period of time during which it is possible to discriminate between tilt operations in a long time of the joystick J and the tilt operation for a short time.

Note that, in the first embodiment or the like, the instruction input unit is configured of the touch panel 14b; however, the instruction input unit may be configured of a joystick J1, and the operation may be performed through a joystick J1.

In the first embodiment or the like, the control unit 12 performs the first display change control with respect to the first image region based on the instruction input when there is an instruction input with respect to the instruction input unit through the first operation method, the control unit 12 performs the second display change control with respect to the second image region based on the instruction input when there is an instruction input with respect to the instruction input unit through the second operation method; however, the control unit is configured to be capable of interchanging the image for performing the display change control through the first operation method based on the instruction input and the image for performing the display change control through the second operation method based on the instruction input and the images for the display change control are interchanged, and thereby the second display change control may be performed with respect to the second image region based on the instruction input when there is an instruction input with respect to the instruction input unit through the first operation method, and the first display change control may be performed with respect to the first image region based on the instruction input when there is an instruction input with respect to the instruction input unit through the second operation method. In other words, when the images for the display change control are interchanged, in the first embodiment and the modification example in the first embodiment, the zoom image region 111 may be operated through the drag operation, and the measurement image region 101 may be operated through the tap operation. In addition, in the second embodiment, Modification Example 1 of the second embodiment, and Modification Example 2 of the second embodiment, the replay image region 211 may be operated through the drag operation, or the live image region 201 may be operated through the tap operation. In addition, in Modification Example 3 of the second embodiment, the position instruction mark image region 311 may be operated through the drag operation, or the live image region 301 may be operated through the tap operation. In addition, in Modification Example 3 of the second embodiment, the position instruction mark image region 311 may be operated not on the live image region 201 but on the replay image region 211.

Note that the first image region and the second image region may be displayed by a single LCD 14a, or may be displayed by a plurality of LCDs 14a.

In Modification Example 2 of the second embodiment, the control target image region and the moving direction are displayed by displaying the movement display image M; however, the control target image region and the moving direction may be displayed by displaying a track of the cursor or the like.

The present invention is not limited to the embodiments described above, and it is possible to perform various modifications, alterations, or the like within a range in which the gist of the present invention does not change.

According to the present invention, it is possible to provide the endoscope device and the method for controlling a display change in the endoscope device that includes a display unit on which a plurality of image regions that display at least one endoscopic image are arranged, enables an instruction input to be performed with respect to the instruction input unit through the predetermined operation method corresponding to the image region, and enables the display change control of the image region to be performed in response to the instruction input.

The invention claimed is:
1. An endoscope device comprising:
 a display; and
 a computer configured to:
   control the display to:
     display a mark image as a first image region; and
     display a live image as a second image region;
   perform first display change control to set a moving direction of the mark image, as the first image region, to control the display to change a display state of the first image region based on an instruction input to an instruction input device through a first operation method; and
   perform second display change control to set the moving direction of the live image, as the second image region, to control the display to change a display state of the second image region based on an instruction input to the instruction input device through a second operation method; and
   in response to receiving an operation instruction, fixing a position of the mark image in the display relative to the live image.

2. The endoscope device according to claim 1, further comprising:
an image sensor configure to capture an image of a subject and to output image data based on the image captured,
wherein the computer is configured to generate an endoscopic image, as the live image, based on the image data output from the image sensor.

3. The endoscope device according to claim 1,
wherein the computer is configured to control the display to display the first image region superimposed on the second image region.

4. The endoscope device according to claim 1,
wherein the computer is configured to control the display to display the first image region at a predetermined transmittance to allow the second image region to transmit through the first image region.

5. The endoscope device according to claim 1,
wherein the computer is configured to:
perform an interchange control to interchange the first image region controlled under the first display change control based on the instruction input through the first operation method with the second image region controlled under the second display change control based on the instruction input through the second operation method, and
following performance of the interchange control,
perform the first display change control to set the moving direction of the live image, as the second image region, to control the display to change the display state of the second image region based on the instruction input through the first operation method; and
perform the second display change control to set the moving direction of the mark image, as the first image region, to control the display to change the display state of the first image region based on the instruction input through the second operation method.

6. The endoscope device according to claim 1, further comprising:
an image sensor configured to capture a plurality of endoscopic images; and
an insertion portion,
wherein the image sensor is arranged to the insertion portion, and
wherein the insertion portion is configured to perform pan/tilt motion,
wherein the second image region is a live image region for displaying the plurality of endoscopic images as the live image as the plurality of endoscopic images are captured,
wherein the computer is configured to perform the second display change control to set the moving direction of the live image, as the second image region, to control the display to change the display state of the second image region to display the plurality of endoscope images as the insertion portion performs pan/tilt motion of the insertion portion based on the instruction input through the second operation method.

7. The endoscope device according to claim 1,
wherein the instruction input device comprises a touch panel,
wherein the first operation method is an operation method in which a first distance from an operation start position to an operation end position on the touch panel is equal to or longer than a predetermined distance, and
wherein the second operation method is an operation method in which a second distance from the operation start position to the operation end position on the touch panel is shorter than the predetermined distance.

8. The endoscope device according to claim 7,
wherein the first operation method is a drag operation on the touch panel, and
wherein the second operation method is a tap operation on the touch panel.

9. The endoscope device according to claim 1,
wherein the instruction input device comprises a joystick,
wherein the first operation method is an operation method in which a period of tilting time per tilt of the joystick is equal to or longer than a predetermined period of time, and
wherein the second operation method is an operation method in which a period of tilting time per tilt of the joystick is shorter than the predetermined period of time.

10. A method comprising:
controlling a display of an endoscope device to:
display a mark image as a first image region; and
display a live image as a second image region;
performing first display change control to set a moving direction of the mark image, as the first image region, to control the display to change a display state of the first image region based on an instruction input to an instruction input device through a first operation method;
perform second display change control to set the moving direction of the live image, as the second image region, to control the display to change a display state of the second image region based on an instruction input to the instruction input device through a second operation method; and
in response to receiving an operation instruction, fixing a position of the mark image in the display relative to the live image.

11. A computer-readable storage device storing instructions that cause a computer to perform at least:
controlling a display of an endoscope device to:
display a mark image as a first image region; and
display a live image as a second image region;
performing first display change control to set a moving direction of the mark image, as the first image region, to control the display to change a display state of the first image region based on an instruction input to an instruction input device through a first operation method;
perform second display change control to set the moving direction of the live image, as the second image region, to control the display to change a display state of the second image region based on an instruction input to the instruction input device through a second operation method; and
in response to receiving an operation instruction, fixing a position of the mark image in the display relative to the live image.

* * * * *